United States Patent [19]
Zoughi et al.

[11] Patent Number: 5,748,003
[45] Date of Patent: May 5, 1998

[54] MICROWAVES USED FOR DETERMINING FATIGUE AND SURFACE CRACK FEATURES ON METAL SURFACES

[75] Inventors: Reza Zoughi, Ft. Collins, Colo.; Chin-Yung Yeh, Taipei, Taiwan; Stoyan I. Ganchev; Christian Huber, both of Ft. Collins, Colo.

[73] Assignee: Colorado State University Research Foundation, Fort Collins, Colo.

[21] Appl. No.: 645,761

[22] Filed: May 14, 1996

Related U.S. Application Data

[63] Continuation-in-part of Ser. No. 459,280, Jun. 2, 1995, abandoned, which is a continuation of Ser. No. 36,941, Mar. 25, 1993, which is a continuation of Ser. No. 960,238, Oct. 13, 1992, Pat. No. 5,216,372, which is a continuation of Ser. No. 737,344, Jul. 29, 1991, abandoned.

[51] Int. Cl.$^6$ .................................................. G01R 27/04
[52] U.S. Cl. .................. 324/644; 324/237; 324/637
[58] Field of Search ............................... 324/644, 237, 324/235; 73/769, 624; 250/308

[56] References Cited

U.S. PATENT DOCUMENTS

| | | | |
|---|---|---|---|
| 3,562,642 | 2/1971 | Hochschild | 324/644 |
| 3,710,243 | 1/1973 | Keenan | 324/644 |
| 4,286,216 | 8/1981 | Auld | 324/237 |
| 4,480,480 | 11/1984 | Scott | 73/769 |
| 5,384,543 | 1/1995 | Bible | 324/644 |

FOREIGN PATENT DOCUMENTS

| | | | |
|---|---|---|---|
| 2269672A | 2/1994 | United Kingdom | G01N 27/00 |

Primary Examiner—Vinh P. Nguyen
Assistant Examiner—Thomas Valone
Attorney, Agent, or Firm—Sheridan Ross P.C.

[57] ABSTRACT

A method and apparatus for determining fatigue/surface crack features on metal surfaces is disclosed wherein the cracks may be empty, filled, or covered with a dielectric (e.g., paint). The present invention includes a microwave waveguide having an aperture for scanning over a surface and thereby characterizing changes in a standing wave within the waveguide when a crack is scanned. In particular, crack related data resulting from standing wave perturbations can be analyzed for determining crack geometric features such as crack width, crack depth, crack length and crack tips. These features are determinable with high precision in comparison to the size of the aperture. When locating and/or sizing the geometric features of a crack, voltage changes induced by higher order modes generated by various orientations of the crack in relation to the aperture are utilized for generating the crack related data. Further, estimates are provided as to the accuracy of a location and/or size estimate for the crack geometric features. The present invention is particularly useful for repair of steel bridges, plains, turbines and other metallic structures subject to surface fatigue cracks.

12 Claims, 19 Drawing Sheets

MICROWAVES USED FOR DETERMINING FATIGUE AND SURFACE CRACK FEATURES ON METAL SURFACES

RELATED APPLICATION INFORMATION

This is a continuation in part of application Ser. No. 08/459,280 filed Jun. 2, 1995, now abandoned, which is a continuation of application Ser. No. 08/036,941, filed Mar. 25, 1993, which is a continuation of application Ser. No. 07/960,238, filed Oct. 13, 1992 and now issued as U.S. Pat. No. 5,216,372, which in turn, is a continuation of application Ser. No. 07/737,344, filed Jul. 29, 1991, now abandoned.

FIELD OF THE INVENTION

The present invention relates generally to devices which employ microwave signals and, in particular, to a novel device which uses the product of transmitted and reflected microwave signals to detect cracks, various crack features or other surface features related to a metallic object of interest. The device can also be used to determine dimensional information regarding the object of interest.

BACKGROUND OF THE INVENTION

In a number of settings, it is desirable to investigate an object which is at least partially comprised of microwave reflective material such as metal to detect certain surface features of the object and/or to determine dimensional information regarding the object. One such detection setting is surface crack detection. Metal fatigue or failure can often be diagnosed through surface crack detection. Such fatigue or failure is of critical importance in many environments, notably including the inspection of aircraft skin and components, nuclear power plant steam generator tubings and steel bridges.

Metal fatigue and subsequent failure usually begins from the surface of the metal. Aircraft fuselage, turbine blades, nuclear power plant steam generator tubing and steel bridges are examples of structures in which this type of metal failure occurs. Hence, surface crack detection on metallic structures is of utmost importance to the on-line and in-service inspections of metallic components. Further, for repair purposes, it is often necessary to know the exact location of the tip of a propagating crack. Although there are many conventional, nondestructive testing methods for detecting surface cracks in metals, it is desirable to have a crack tip location technique for accurately locating crack tips in a simple, straight forward and real time manner, including in cases where the crack is covered or filled in by a material, such as paint.

Accordingly, many surface crack detection techniques have been investigated or developed, including acoustic emission, dye penetrant, eddy current, ultrasonic, radiography (using x-ray or gamma radiation), magnetic particle, and microwave mode conversion testing. Each of these techniques is subject to one or more of the following limitations: they require complicated instrumentation or numerical analysis which makes the subject equipment expensive and unacceptable for certain applications; surface contact is required which is not practical in all environments; their applicability is temperature dependent; their sensitivity may be unacceptably affected by dirt, paint, rust or the like covering the surface under examination; they introduce a danger of damage, e.g., arc burns, to the surface under examination; they are unacceptably sensitive to material permeability or metal type; they require significant operator expertise; their sensitivity is limited to cracks of a particular size range; they are not readily adapted for use on surfaces of various shapes; and/or they do not allow for testing of large surface areas in a short period of time. There is thus a need for an improved crack detection apparatus.

An example of a setting where dimensional information regarding an object is desired is in measuring the thickness of rubber on a steel-belted tire. As used herein, dimensional information broadly includes information relating to the position, shape, size, orientation and internal structure or spatial relationships of an object. Reference is made to U.S. Pat. No. 5,216,372 for details of a microwave steel belt location sensor for tires.

It will be appreciated that many other examples of settings were it is desired to detect surface features of an object or obtain dimensional information regarding an object are possible. Generally, in such settings, there is a need for a reliable and inexpensive detector which is easy to use and is not subject to problems and limitations such as discussed above.

SUMMARY OF THE INVENTION

The present invention discloses devices useful for detecting surface features of and/or determining dimensional information regarding objects at least partially comprised of microwave reflective material. The present invention has a number of advantages over conventional devices including ease of use, simplified data processing, rapid information return and a broad range of applicability.

According to the present invention, surface feature detection or dimensional information acquisition is accomplished by reflecting a microwave signal off of an object of interest, combining the incident and reflected microwave signals to produce a resulting signal (i.e., a standing wave), and analyzing the resulting signal to yield the desired detection or dimensional information. An apparatus constructed in accordance with the present invention thus includes a microwave signal source, a structure for receiving the incident and reflected signals such that the signals interact therein to produce the resulting signal, and an analyzer for analyzing the resulting signal. The structure for receiving the signals preferably comprises a circular or rectangular waveguide. The analyzer can include a sensor disposed within the waveguide for measuring $E_x$ or $E_y$ and associated signal processing components.

In one embodiment, an apparatus for use in detecting and measuring cracks in a metal surface is provided. The apparatus comprises a source for transmitting a first microwave signal, an open ended waveguide and a sensor such as a crystal diode for measuring a local electric field. The open end of the waveguide is positionable adjacent the surface to be tested. The waveguide is operative for receiving a first signal from the signal source and receiving a second signal reflected off of the surface such that interference between the signals results in a standing wave in the waveguide. The sensor can be utilized to sense movement of the standing wave, e.g., due to the presence of a surface crack within the open end of the waveguide as the waveguide is scanned over the surface, thereby providing for crack detection and measurement. Scanning can be performed manually or can be motorized.

The crack detection apparatus of the present invention has a number of advantages. First, the apparatus need not be in contact with the surface under examination, thus providing significant operational flexibility. In addition, the apparatus can be used in high or low temperature environments and is useful even if the crack is filled or covered by dielectric materials such as dirt, paint or rust. Moreover, the apparatus does not require great user expertise and can be arranged in a multiple waveguide array format to allow for scanning of large surface areas in a short time. The apparatus can also be used on curved surfaces such as tubings.

In a related embodiment, the present invention includes a method and apparatus for detecting and locating surface crack features of non-ferromagnetic and ferromagnetic metals and alloys, as well as on the surface of graphite composite materials wherein the cracks may be empty, filled or covered with a dielectric (e.g., paint). That is, the present invention may be utilized in detecting surface crack tips in highly conducting media, such as metals, where microwave signals undergo a substantially complete reflection at the surface, and hence expose only surface perturbations such as fatigue/surface cracks. More particularly, the present invention generates crack related data resulting from standing-wave perturbations within the waveguide that may be analyzed for determining crack geometric features such as crack width, crack depth, crack length and crack tips. Moreover, these features can be determined with high precision in comparison to the size of the waveguide aperture. When locating and/or sizing the geometric features of a crack, voltage changes induced by higher order modes generated by various orientations of the crack in relation to the aperture are utilized for generating the crack related data. Further, estimates are provided as to the accuracy of a location and/or size estimate for the crack geometric features.

To locate such crack geometric features with the present invention, it has been observed that the smooth surfaces of highly conducting media are a fairly good short circuit load for the waveguide. However, when a surface crack is exposed to the signals from the waveguide, higher order signal wave modes are generated or reflected by the crack, and the properties of the wave reflected into the waveguide will be different from those of the short circuit load provided by an exposed surface not having a crack. Therefore, by strategically probing the standing wave pattern induced inside the waveguide, as a cracked surface is scanned, information about both the existence of a crack and its geometric features may be obtained.

Furthermore, it is an aspect of the present embodiment of the invention (for detecting and locating surface crack features) to provide a method for iteratively scanning across a crack for generating a two-dimensional image that can be used for identifying a crack tip. Alternatively, in a closely related embodiment of the present invention, the scanning may be performed solely along the length of the crack for generating a signal or graph that may be used to effectively determine a crack tip and/or crack length.

DETAILED DESCRIPTION

The detectors of the present invention use the product of a transmitted microwave signal and a reflected microwave signal to detect cracks or other surface features of an object which is at least partially comprised of microwave reflective material. As described below, the detectors can also be used to determine dimensional information regarding such an object. The transmitted and reflected signals interact within an appropriate waveguide to form a resulting signal, e.g., a standing wave. The characteristics of or changes in the resulting signal can then be analyzed in accordance with mathematical models to provide the desired detection or dimensional information.

In the following description, the invention will be described in connection with two environments; surface crack detection or sizing and tire tread thickness measurement. However, upon consideration of the present disclosure, it will be appreciated that the subject invention is more generally useful in a broad range of detection applications. The embodiments described below are therefore intended to be exemplary.

Surface Crack Detection

In a situation where an electromagnetic wave impinges upon a plane of conductive material, the wave is reflected. Assuming the direction of propagation of the wave is normal to the conductive plane, the plane is unflawed and the plane is a perfect conductor, the wave will be completely reflected normal to the conductive plane. If the transmitted or incident wave and the reflected wave are permitted to interact within a waveguide, interference between the waves traveling in opposite directions results in a standing wave.

A different situation is presented where the reflecting surface is not flat, i.e., is disturbed by a crack, bulge or other disturbance. In such situations, higher order modes are generated which change the reflection properties of the reflected wave. This, in turn, results in a perturbation in the standing wave which is indicative of the presence and dimensional features of the crack or other disturbance. The standing wave can thus be analyzed to yield crack detection and measurement information.

Figure 1:
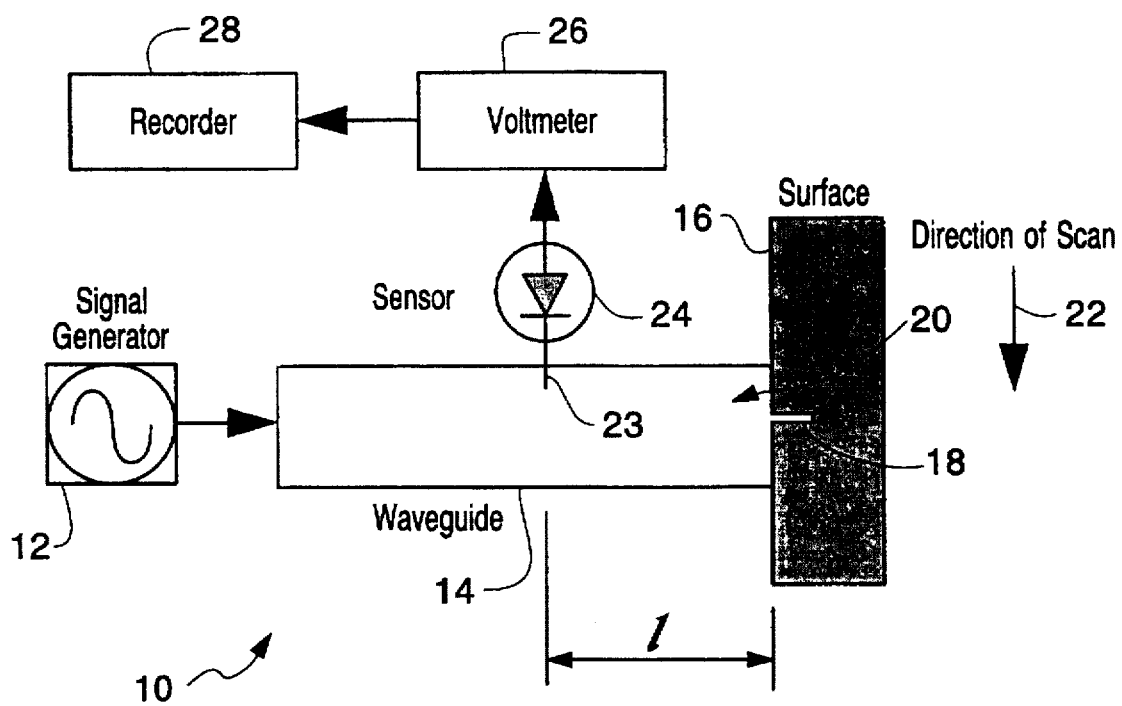
FIG. 1 is a schematic diagram showing the major components of a surface crack detector constructed in accordance with the present invention.

Referring to FIGS. 1 and 2, a surface crack detector constructed in accordance with the present invention is generally identified by the reference number 10. A signal generator 12 produces a microwave signal that is directed by a waveguide 14 towards the surface 16 to be analyzed. One purpose of the illustrated detector 10 is to detect cracks 18 in the surface 16. The detector can also be used to measure cracks 18 as will be described below.

The frequency of the incident microwave signal can be selected based on the desired measurement sensitivity of measure. In particular, cracks 18 which are a fraction of a millimeter width can be easily detected at frequencies of about 20 GHz or lower. Higher frequencies can be used to detect smaller cracks. The signal generator 12 thus comprises an oscillator capable of providing a microwave signal of the selected frequency. In the illustrated embodiment, the signal generator 12 comprises a conventional oscillator for providing a 24 GHz microwave signal.

Figure 2A:
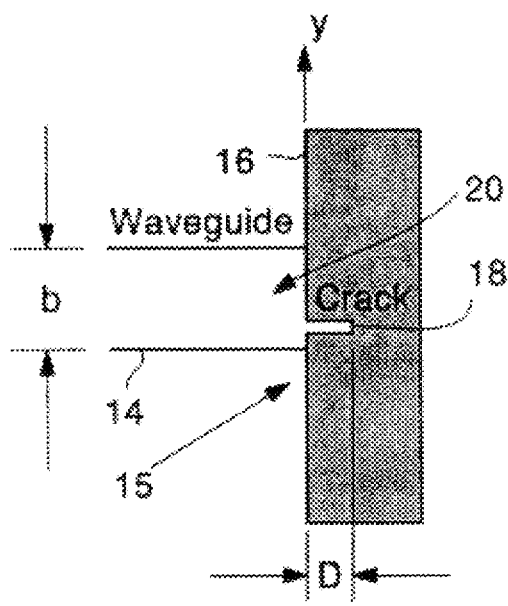
FIG. 2A is a side view showing a portion of the surface crack detector of FIG. 1 positioned on a cracked surface.
Figure 2B:
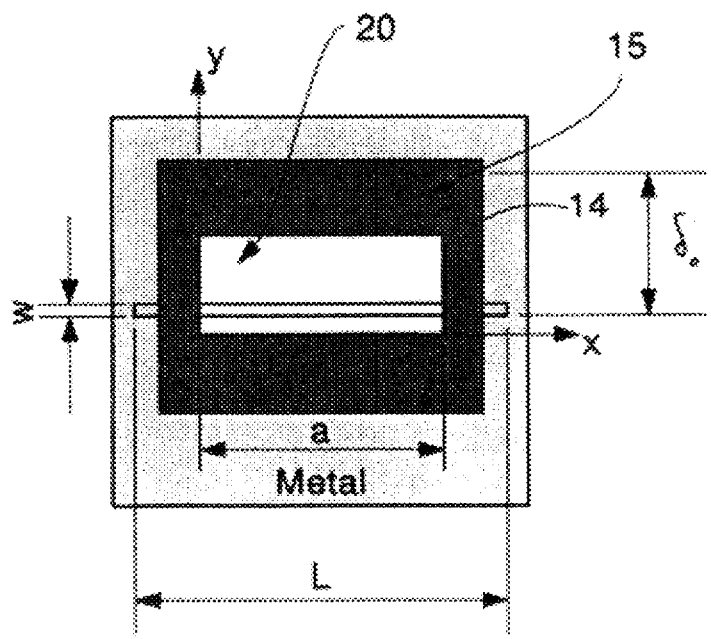
FIG. 2B is a front view showing a portion of the surface crack detector of FIG. 1 positioned on a cracked surface.

In principle, a variety of different types of waveguides including, for example, both circular and rectangular waveguides, can be satisfactorily utilized in detector 10. In this regard, circular waveguides may be preferred for certain applications because crack detection becomes independent of crack orientation. The illustrated waveguide, as shown in FIGS. 2A and 2B, is a K-band slotted rectangular waveguide (a=10.67 mm and b=4.32 mm), which operates in its dominate $TE_{10}$ mode. Waveguide flange 15 is useful in guiding the waveguide 14 along the surface 16. It will be appreciated that the flange 15 and aperture 20 can be formed to facilitate scanning of curved surfaces such as tubings.

In operation, the aperture 20 of waveguide 14 is manually or mechanically scanned across surface 16 in a direction transverse to crack 18 as generally indicated by arrow 22. When the crack 18 is not within the aperture 20 of waveguide 14, the microwave signal is substantially completely reflected off of surface 16, as noted above, and interference between the incident and reflected signals results in creation of a standing wave in waveguide 14. As the scan continues and crack 18 enters aperture 20 of waveguide 14, higher order modes are generated in the reflected signal as experienced in waveguide 14. As a result, the standing wave in waveguide 14 shifts relative to the flat surface scenario described above. As the crack 18 exits aperture 20 of waveguide 14, the flat surface conditions are restored and the standing wave in waveguide 14 returns to the position described initially.

It is possible to sense this shifting of the standing wave using a single probe disposed within waveguide 14 for measuring an electromagnetic field in the waveguide 14, though more than one such probe may of course be utilized to accurately monitor standing wave shifts. The illustrated detector 10 employs a single probe 23 connected to a sensor 24 wherein the sensor 24 may include a conventional crystal diode for measuring the local electric field, wherein the probe 23 is positioned a distance, 1, from aperture 20.

It will be appreciated that the standing wave characteristics generally vary in a sinusoidal manner with respect to probe 23 position relative to aperture 20. As a consequence, the magnitude of the detected change in standing wave characteristics for a given wave shift is dependent on probe 23 location. The distance, 1, can thus be selected to enhance detector 10 sensitivity. The illustrated probe 23 is positioned 9.48 cm from aperture 20. The probe 23 and sensor 24 output is preferably obtained while scanning, via conventional voltmeter 26 and recorder 28, to provide information for each surface scan. However, it will be appreciated that mere observation of voltmeter 26 movement is sufficient for crack 18 detection.

Figure 3:
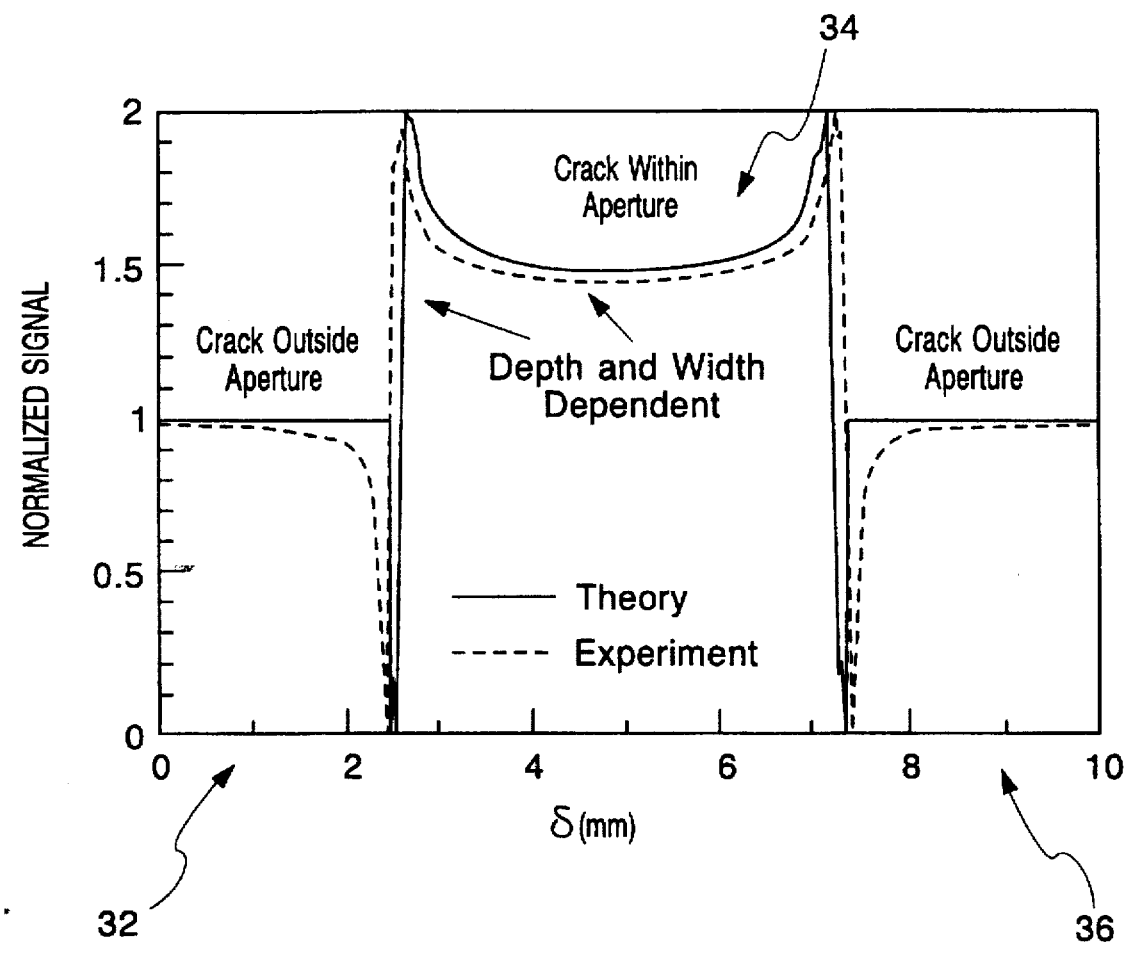
FIG. 3 presents the graphs comparing the theoretically predicted characteristic curve for a scan over a surface crack and corresponding experimentally determined data.

Referring to FIG. 3, the crack detection technique as described above can be modeled mathematically. For the purposes of demonstrating the theoretical foundation of the present invention, the theoretically predicted detector output was compared to experimental results for a scan of a crack 18 having a length, L, of 20.1 mm, a width, W, of 0.9 mm, and a depth, D, of 1.45 mm. That is, assuming the crack 18 is substantially parallel to the wider dimension, a, of the aperture 20 (as in FIG. 2B), the graphs of FIG. 3 illustrate two variations of what hereinafter is referred to as a "crack characteristic signal" provided by the sensor 24 as voltage variations related to crack offset, δ, as shown in FIG. 2B. In particular, the graph of each crack characteristic signal includes the following features:

(1.1) An initial portion 32 corresponding to a voltage measurement wherein the crack is not (entirely) within the aperture 20 (e.g., the crack is either outside the aperture or substantially coincident with the broad side of the aperture (underneath or extremely close to the waveguide edge that defines the aperture;

(1.2) A middle portion 34 wherein the crack has a segment that is contained in the aperture and the segment extends the entire length of the broad dimension;

(1.3) A trailing portion 36 wherein the crack is either outside of the aperture or coincident with a broad dimension boundary of the aperture (underneath or extremely close to the waveguide edge that defines the aperture); and (1.4) A abrupt signal change between each of the graph portions 32–36 wherein the initial and trailing portions dip and the middle portion include a center "U" shape.

Notwithstanding these general features, note that a crack characteristic signal is unique for: (i) a given set of crack dimensions (e.g., width and depth); (ii) a waveguide 14 operating frequency; and (iii) the dimensions of the waveguide 14. Additionally, note that these graphs have been "normalized" with respect to the voltage detected when the crack 18 is outside of the waveguide aperture 20. That is, the voltage detected when the crack 18 is outside of the aperture 20 is is that of a short circuit case.

For the theoretical analysis corresponding to the theoretical crack characteristic signal of FIG. 3, a flat plate was modeled as the surface 16 wherein the waveguide 14 terminated in a short circuit. The configuration where the crack 18 is within the waveguide aperture 20 was modeled as a large waveguide feeding a much smaller short circuited waveguide, where each waveguide had the same broad dimension, a. The solid line trace of FIG. 3 was mathematically obtained by solving known electromagnetic field equations relative to the boundary conditions appropriate for the cases where the crack 18 is: (i) outside the waveguide aperture 20, (ii) partially within the aperture 20 (e.g., coincident with an aperture 20 broad dimension boundary), and (iii) has a crack segment that is both entirely within the aperture 20 and extends the entire length of the broad dimension of the aperture (this last condition hereinafter simply referred to as the crack being "fully within the aperture") fully within the aperture 20. For the experimentally determined graph, data points are shown as dots in FIG. 3, thus demonstrating good agreement with the theoretical model.

The surface crack detector 10 can be used for crack measurement in addition to crack detection. Referring again to FIG. 3, the crack width is related to features of the illustrated characteristic curve, which includes a pair of dips and peaks corresponding to the crack edges. The crack width can thus be determined by mathematically analyzing the characteristic curves or by calibrating the features of the characteristic curves relative to a library of empirically derived data. In this regard, referring to FIG. 3, it has been observed that for shallow cracks, the crack width is approximately given by the equation:

$$W = \frac{(p+p')}{2} - b \quad (1)$$

where p is the distance between the dip minima, p' is the distance between the two turning points (defined as the points of separation between the characteristic curve and lines 30 drawn through the minima tangent to the characteristic curve) and b is the width of the waveguide aperture 20 (as shown in FIG. 2A). This is an approximation since the depth of the crack has some influence on the width value.

Figure 15:
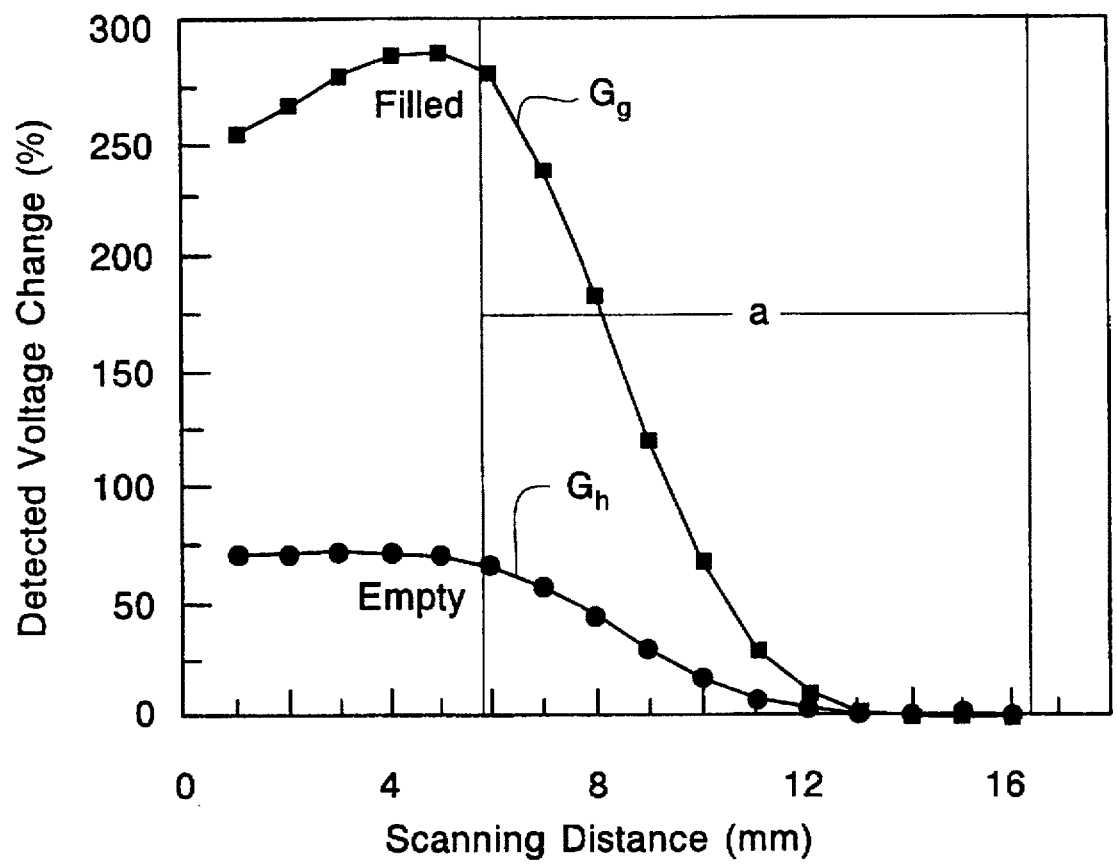
FIG. 15 presents the crack tip characteristic signal graph for an empty crack and another for a filled (with beeswax) crack, the cracks otherwise being identical, with a width of W=0.3 mm and a depth of a D=2 mm at 24 GHz.

Additionally, the crack detector 10 can be used to determine crack depth. The two graphs of FIG. 15 represent the crack characteristic signals for two different cracks 18. In particular, the graph 37 is for a crack having a width of W=0.28 mm and depth of D=1.49 mm and the graph 38 is for a crack having the same width but a depth of D=0.96 mm. Further, the graphs of FIG. 15 are for an operating frequency of 24 GHz. Note, as will be demonstrated hereinbelow, that the difference between the signal levels in the middle portion 34 of the crack characteristic signal graphs can be used for crack depth determination as well as for crack width determination as discussed above.

Figure 4A:
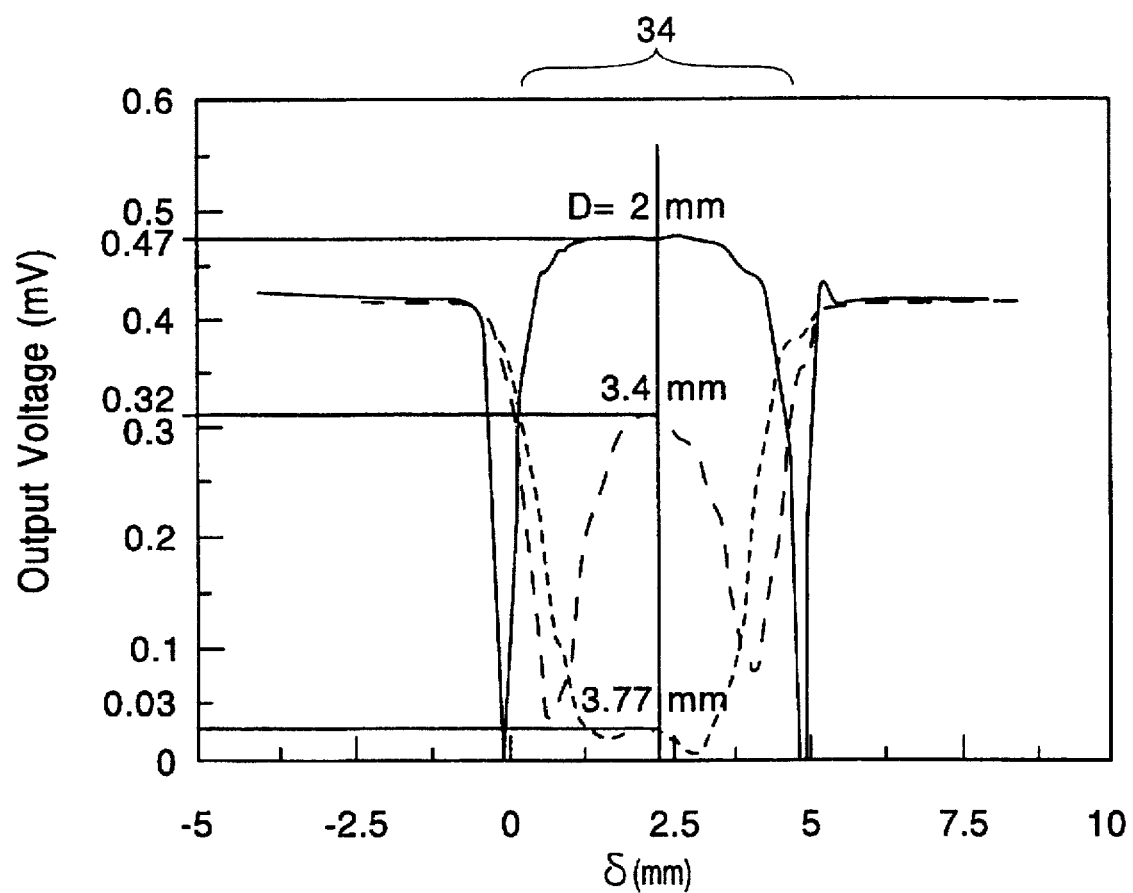
FIG. 4A presents graphs showing the characteristic curves for scans over cracks of different depths.

Referring to FIG. 4A, there are shown three characteristic curves corresponding to cracks of three different depths (2 mm, 3.4 mm and 3.77 mm). As FIG. 4B demonstrates, the shape of the characteristic curves in the region corresponding to presence of a crack within the waveguide aperture 20, is dependent upon crack depth and width. Accordingly, by calibrating the characteristic curves relative to empirically derived data, or by mathematically modeling the characteristic curves as a function of crack depth and width, crack depth information can be provided.

Calibration of the characteristic curves or sensor output to yield crack depth information can be accomplished in a variety of ways. For example, the relationship between the sensor output for a particular scan location corresponding crack depth (for cracks of a specified width and length) can be determined empirically. In this regard, the scan location utilized for calibration can be selected to correspond to particular features of the characteristic curves, such as dips or peaks, or the scan location can be an arbitrarily selected location.

Figure 4B:
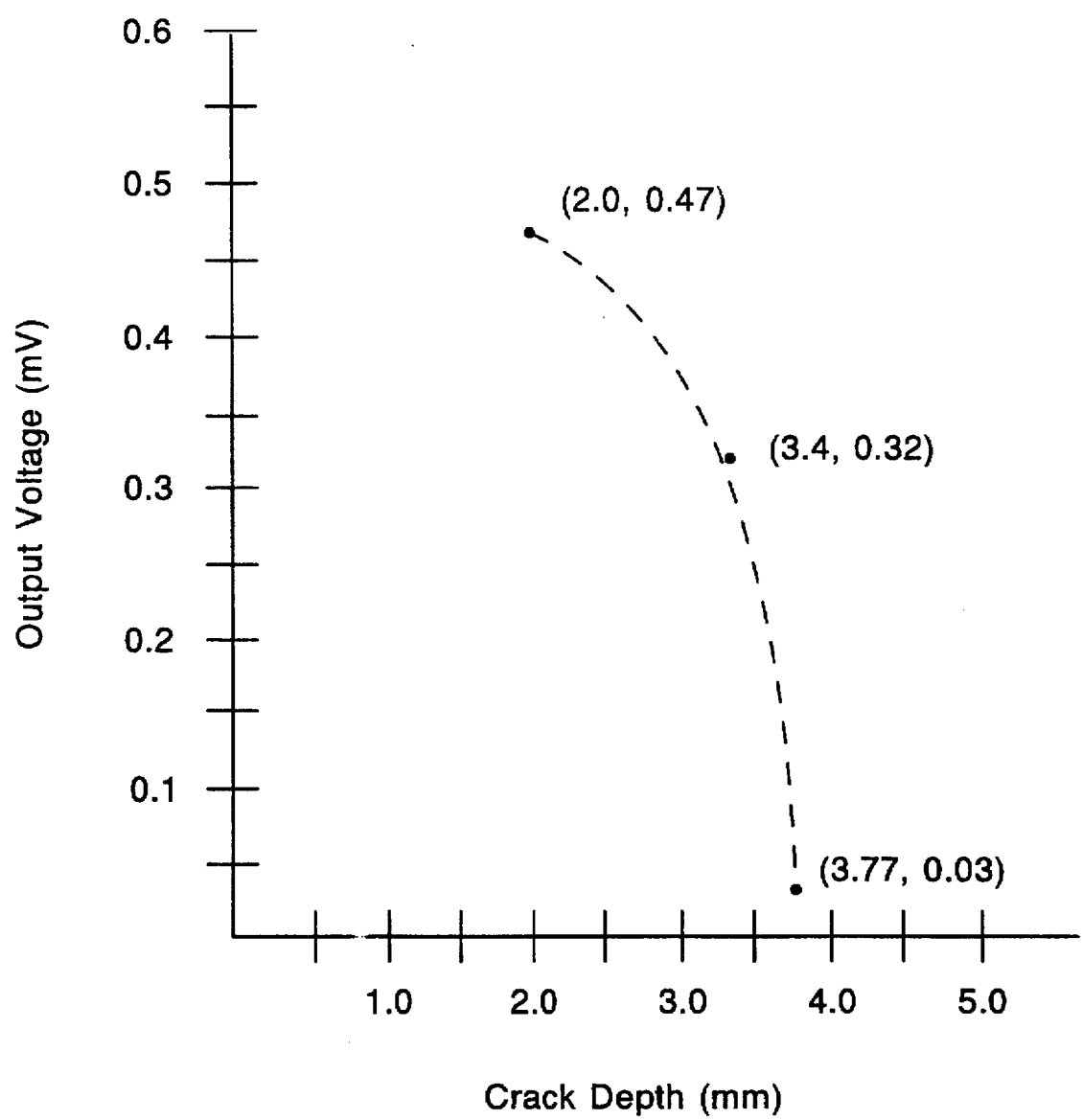
FIG. 4B is a graph illustrating one method for calibrating crack depth based on sensor output.

One such calibration technique is illustrated in FIGS. 4A and 4B. The scan location selected for calibration in this example was δ=2.5 mm. As shown in FIG. 4A, three data points representing the sensor output voltage for three different crack depths were obtained, where each of the cracks had an identical width and a length which extended completely across the waveguide aperture 20. In particular, for crack depths of 3.77 mm, 3.4 mm and 2 mm, sensor outputs of approximately 0.03 mV, 0.32 mV and 0.477 mV, respectively, were obtained. These three data points were plotted graphically as shown in FIG. B. A curve was then fitted to the data points for use in estimating unknown crack depths, for cracks of the specified width and length, based on the sensor output at δ=2.5 mm.

It should be appreciated that this simple example is presented for illustration purposes. In practice, it is expected that many such data points would be required for accurate calibration. In addition, other types of data, such as an area defined by a characteristic curve and a reference voltage line, may be used in place of output voltage at a particular scan location. Moreover, the characteristic curve shape is dependent upon crack length and width as well as crack depth. Accordingly, calibration may include consideration of crack width and length in conjunction with crack depth, thereby providing a large library of calibration information.

As previously noted, crack depth can also be determined mathematically. Using an open-ended rectangular waveguide with dimensions a and b to detect a crack with width W and depth D, the reflection coefficient for the dominant mode, $TE_{10}$, can be approximately and in a general way expressed as:

$$\Gamma \cong \frac{\frac{W}{b} + j\cot\beta_1 D}{\frac{W}{b} - j\cot\beta_1 D} \quad (2)$$

Figure 4C:
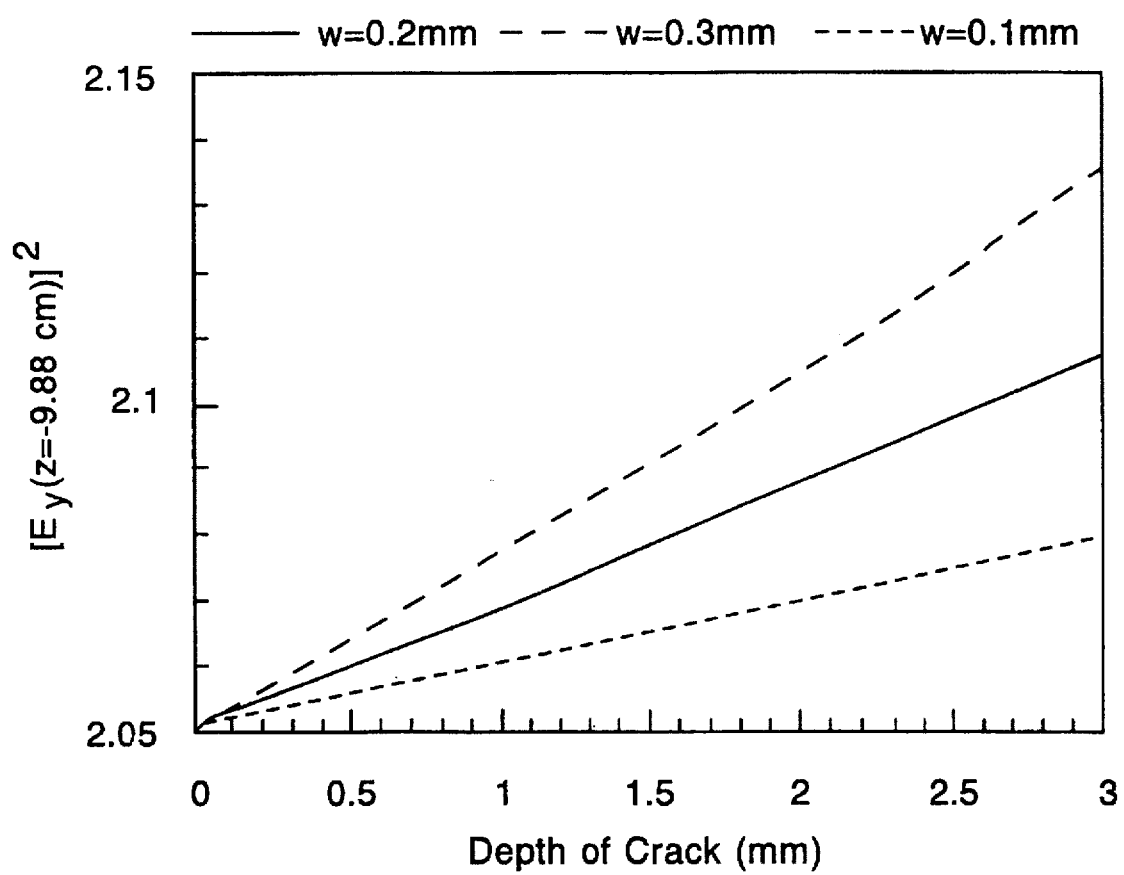
FIG. 4C presents graphs illustrating a mathematically based method for crack sizing.

Then the total $E_y$-field of the dominant mode is $$E_y = \sin\frac{\pi x}{a} e^{-j\beta_1 z} + \Gamma \sin\frac{\pi x}{a} e^{j\beta_1 z} \quad (3)$$

and the approximate value of $|E_y|^2$ can be plotted as a function of W and D for sizing the detected crack, as shown in FIG. 4C. Using the method described above in discussing FIG. 3, the width W of the crack can be estimated from the crack characteristic signal. Knowing the crack width, the crack depth can be determined as a function of $|E_y|^2$ by using plotted curves such as shown in FIG. 4C. Conversely, if the crack depth is known, the width can be determined according to the same mathematical principles.

In the preceding description, the probe 23 was assumed to project from one of the two major walls of rectangular waveguide 14 so as to measure $E_y$. It is also possible to detect surface cracks 18 based on measurements of $E_x$, where $E_x$ is oriented perpendicular to $E_y$. As previously noted, in the absence of a crack 18, the incident microwave signal will be substantially completely reflected so that substantially the entire reflected signal back propagates through the waveguide. However, in the presence of a crack 18, higher order modes as indicated by fluctuations of $E_x$ are generated. Although these modes attenuate rapidly, they can be detected very near the crack. Because these higher order modes only occur when a crack 18 is present, measurements of $E_x$ can yield positive and highly sensitive crack detection.

Figure 5:
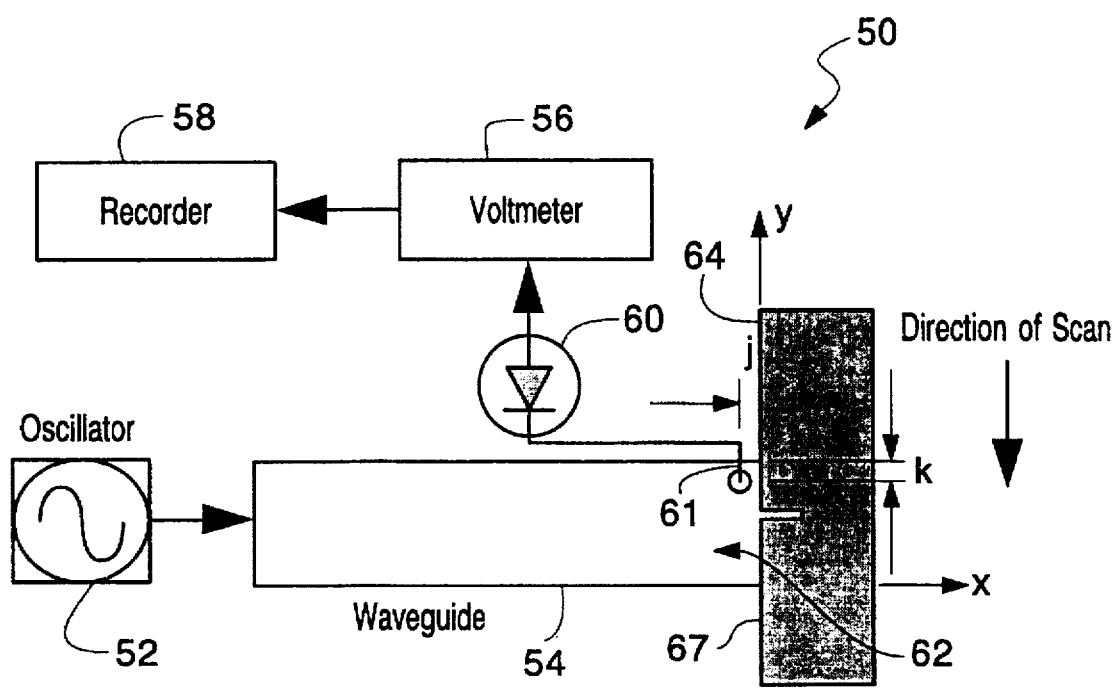
FIG. 5 is a schematic diagram showing the major components of a surface crack detector constructed in accordance with an alternative embodiment of the present invention.

A surface crack detector 50 for detecting cracks based on measurements of $E_x$ is shown in FIG. 5. The detector 50 includes a signal generator 52, a waveguide 54, a voltmeter 56 and a recorder 58, which can be identical to the corresponding components described above.

The detector 50 further includes a sensor 60 which is adapted for measuring $E_x$. In this regard, the sensor 60 is connected to a probe 61 that is disposed in close proximity to the crack and can be placed immediately adjacent aperture 62 of waveguide 54. The illustrated probe 61 is positioned a distance, j, of about 0.2 mm from aperture 62 within waveguide 54. Additionally, the probe 61 projects from one of the two minor walls of waveguide 54 so as to measure $E_x$. Crack detection is accomplished as described above by scanning the waveguide aperture 62 across a surface 64 to be tested while monitoring the sensor 60 output. Waveguide flange 67 and the shape of aperture 62 assist in maintaining a perpendicular orientation of the waveguide 54 relative to surface 64 during scanning.

Figure 6:
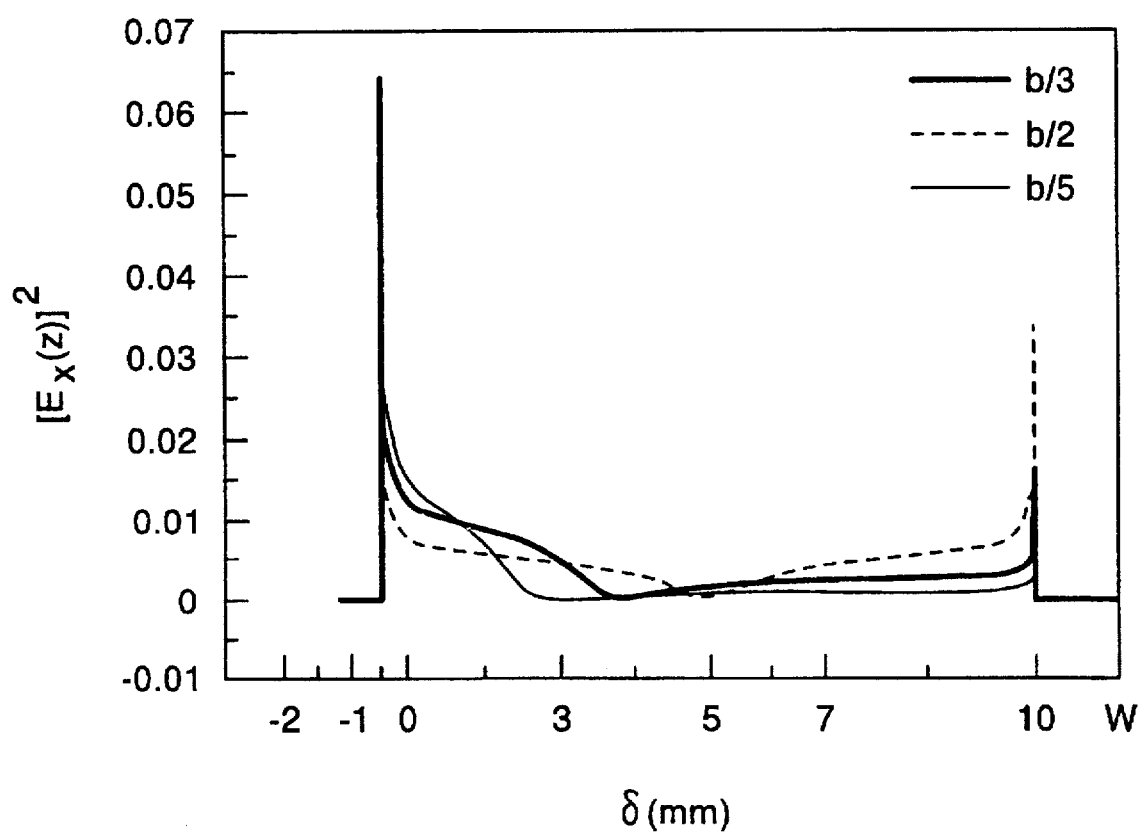
FIG. 6 shows theoretical curves illustrating the effect of sensor placement on sensor output.

The distance k of separation between the probe 61 and the wall of waveguide 54 can also be selected to enhance crack detection. This effect is shown by the three theoretically derived characteristic curves illustrated in FIG. 6. The three curves, in which scanning location δ is plotted against $E_x^2$, correspond to sensor positions of k=b/2 (dashed curve), k=b/3 (thick solid line) and k=b/5 (thin solid curve) where b is the minor dimension of rectangular waveguide 54. The curves are based on a signal frequency of 12.4 GHz, a waveguide aperture of a=22.86 mm by b=10.16 mm, and a crack size of width=0.14 mm by depth=1.2 mm.

As shown, when the crack 18 is outside of the waveguide aperture 62 (δ<0 or δ>10.16 mm), $E_x^2$ is zero. When the crack is inside of the aperture (0<δ<10.16 mm), the maximum value of $E_x^2$ depends upon the position of probe 61. The positioning of probe 61 can thus be selected to provide the largest obtainable maximum value of $E_x^2$, thereby enhancing detector signal-to-noise ratio. In this regard, the illustrated probe 61 is positioned at approximately k=b/6 which provides excellent detection for the specified signal frequency and corresponding waveguide dimensions. Other values of k will be optimal for other signal frequencies.

Figure 7:
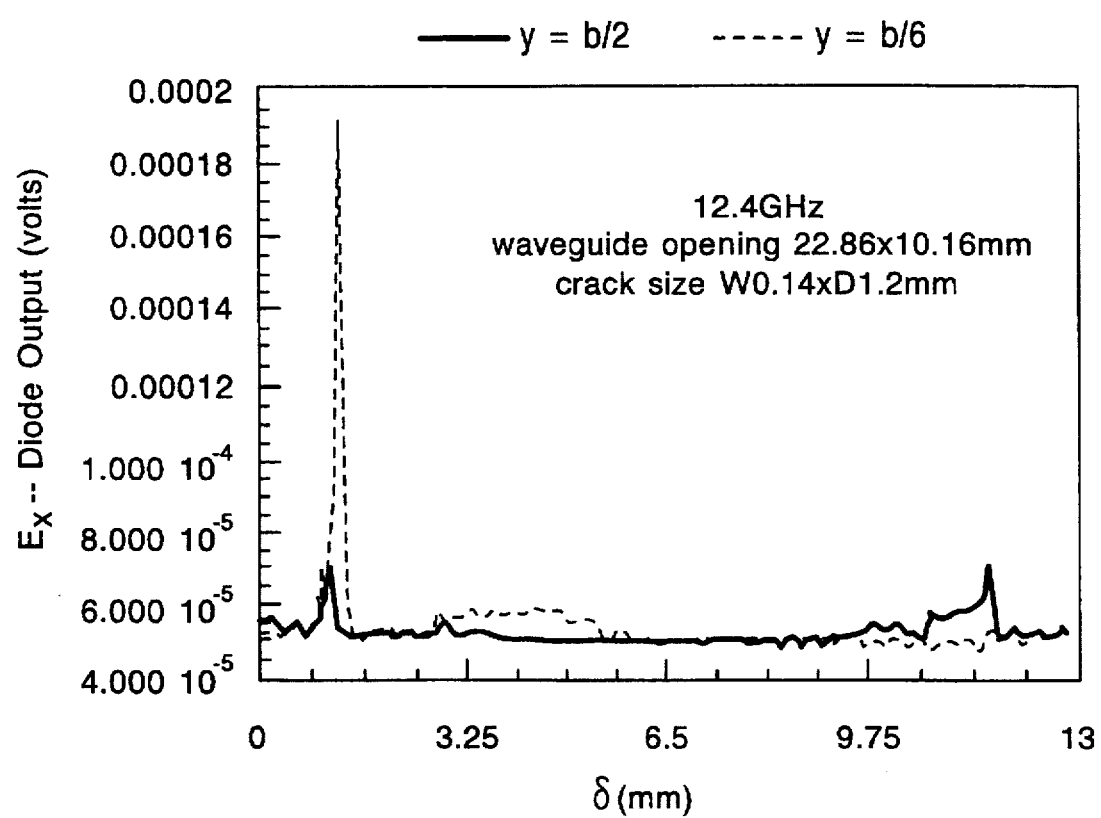
FIG. 7 shows experimentally obtained signals illustrating the higher detection sensitivity achieved by appropriate sensor placement.
Figure 8:
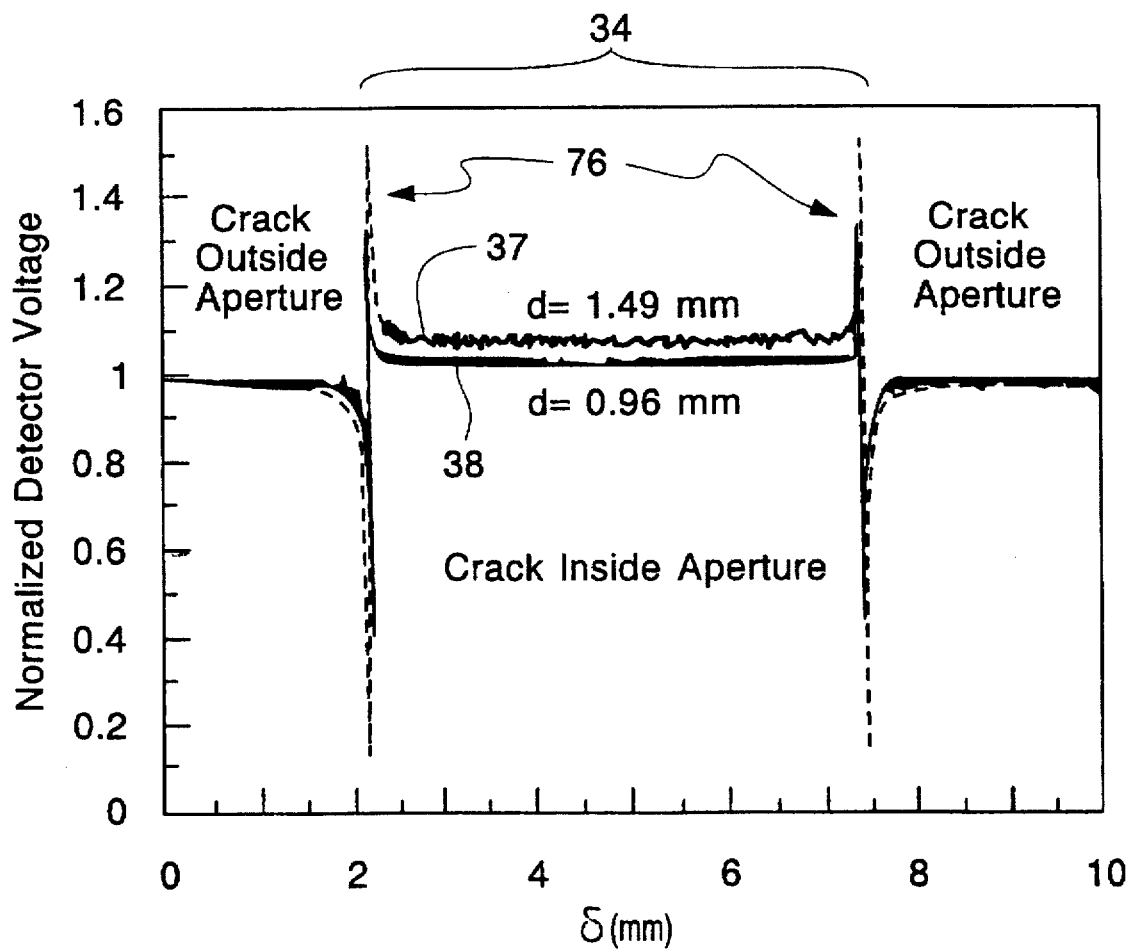
FIG. 8 presents the graphs of two experimentally obtained crack characteristic signals for identical cracks except for differing crack depths.

FIG. 7 illustrates experimentally the increase in detection sensitivity which can be achieved by appropriate positioning of the probe 61. The dashed signal in FIG. 7 was experimentally obtained with the probe 61 positioned at k=b/6 and the solid signal was obtained with the probe 61 positioned at k=b/2. The microwave signal (12.4 GHz), waveguide dimensions (22.86×10.16 mm) and crack size of width 0.14 and depth 1.2 mm was used to obtain the experimental signals of FIG. 7 were identical to the values employed to obtain the theoretical curves of FIG. 6. By comparing the experimental signals of FIG. 7 to the corresponding theoretical curves of FIG. 6, it can be observed that the experimental signal for the sensor position k=b/2 is somewhat obscured by noise and is more difficult to ascertain than for k=b/6. However, the experimental signal for k=b/6 includes a well-defined spike thereby yielding positive crack detection.

Although the crack detectors of the present invention have been described in connection with exemplary embodiments including a single $E_y$ sensor or a single $E_x$ sensor, it will be appreciated that any number of $E_x$ and/or $E_y$ sensors may be employed in a single detector to yield crack information.

Using, for example, the apparatus of FIG. 1 (although the apparatus of FIG. 5 could also be used), the present invention also provides for determining a crack length by locating the tips of a crack. In particular, the present invention can accurately locate a crack tip using a relatively large aperture 20 and even when the crack tip is covered by a material.

In discussing the techniques for identifying a crack tip location, it is important to note (as is discussed further hereinbelow) that the signal level detected by the sensor 24 when the crack 18 is inside the waveguide aperture 20 is a function of crack depth and width (in that order of importance). Furthermore, referring to the graphs of FIG. 15, the distance or length of the middle portion 34 between the two sharp transitions is a function of the narrow dimension, b, of the aperture 20 and the width of the crack 18 (the depth influences this dimension as well but less significantly) as discussed in relation to FIG. 3. Also note, as discussed hereinbelow, that when the crack 18 extends entirely across the wider or broad dimension, a, of the aperture 20 and the crack 18 is away from the edges of the waveguide 14, then the detected signal level within the waveguide remains substantially constant.

The present invention includes two modes for determining a crack tip location. The first mode includes scanning a crack 18 in two different directions and thereby producing an electronic two dimensional image of the crack. The second mode includes scanning the crack 18 only in a single direction for determining a crack tip location.

Figure 9A:
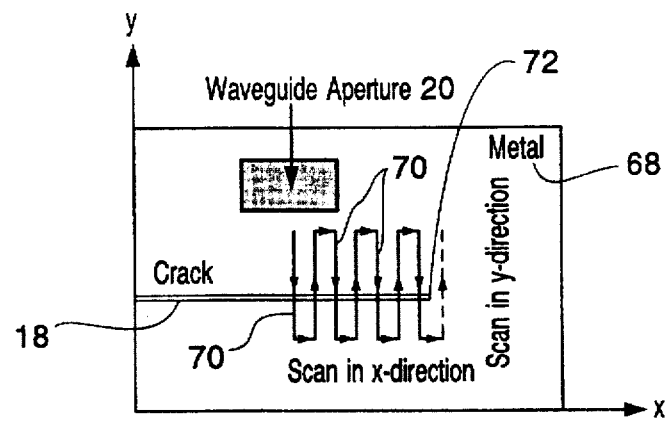
FIGS. 9A–9D illustrate the movement of the waveguide aperture over a surface for locating a crack tip.

FIG. 9A illustrates the first mode for determining a crack tip location, wherein the crack 18 has been located via, for example, the techniques described above. That is, assuming the crack 18 is in a metal specimen 68, in this first embodiment the waveguide aperture 20 is scanned over the specimen 68 in a raster fashion along the x and y directions as shown. Scanning in this manner results in a two dimensional image of the crack 18. That is, with each scan 70 of the crack 18 in the y direction by the waveguide aperture 20, a crack characteristic signal similar to those represented in FIGS. 3 and 4 is generated. As the scanning proceeds in the x direction, the crack tip 72 begins to enter the waveguide aperture 20 as shown in FIG. 9C (where the crack tip 72 is inside the aperture by $δ_1$). As the scanning continues further, the configuration of FIG. 9D occurs where the crack tip 72 is about to leave the aperture 20. Thus, by imaging the scans 70 in their sequential order heading towards the crack tip 72, and imaging higher normalized detector voltages as darker, a two dimensional image such as those of FIGS. 10A and 10B are generated of the crack 18. Note that the middle portion 34 of the graphs of FIG. 3 corresponds to the heights 74 in FIGS. 10A and 10B, and the discontinuities 76 (FIG. 3) correspond to the dark substantially horizontal boundary lines 78 in FIGS. 10A and 10B.

When the crack 18 fully traverses the broad dimension, a, of the waveguide aperture 20, the dominant $TE_{10}$ mode in the waveguide 14 and in the crack 18 are the same, as one skilled in the art will appreciate, wherein the electric and magnetic fields for $TE_{10}$ are given by $$E_y^i = \sin\frac{\pi x}{a} e^{-j\beta_1 z} \quad (4)$$

$$H_x^i = \frac{-1}{\eta_1} \sin\frac{\pi x}{a} e^{-j\beta_1 z} \quad (5)$$

where $$\beta_1 = \sqrt{k_0^2 - \left(\frac{\pi}{a}\right)^2} \;,\; k_0 = \frac{2\pi}{\lambda_0} \;,\; \eta_1 = \frac{k_0\eta_0}{\beta_1} \;,\; \eta_0 = \sqrt{\frac{\mu_0}{\epsilon_0}} \quad (6)$$

and where $\lambda_0$, $\kappa_0$, $\eta_0$ and $\mu_0$ are the free-space wavelength, wavenumber, permittivity and permeability, respectively. $\eta_0$ and $\eta_1$ are the free-space and waveguide intrinsic impedances, respectively. It is believed that the dominant $TE_{10}$ mode in the waveguide 14 and the crack 18 are identical due to the fact that the length of the crack within the aperture 20 is equal to the broad dimension, a, of the waveguide. However, when the crack tip 72 enters the waveguide aperture 20, the dominant mode in the crack 18 is no longer the same as that of the waveguide 14. Thus, there is a relatively significant and abrupt influence on the crack characteristic signal. Further, as the crack tip 72 traverses the broad dimension, a, of the aperture 20, the crack characteristic signal from each scan 70 gradually changes until the crack 18 is entirely outside the aperture 20 in which case a constant voltage is thereby detected (this being a short circuit load).

The image of FIG. 10A was in fact generated from the first mode for determining a crack tip location as discussed above. In particular, FIG. 10A is an image of a crack 18 (more precisely, a slot) milled on an aluminum plate 68 with a width of 0.3 mm and a depth of 2 mm and imaged using signals at a frequency of 24 GHz and with aperture 20 having dimensions of a=10.67 mm and b=4.32 mm. The crack tip 72 in this case was produced by tightly filling one end of the slot 18 with a conducting shim (not shown).

The image of FIG. 10B was also generated using the first embodiment for determining a crack tip location. However, in this case the slot 18 of FIG. 10A was filled with beeswax (which has a dielectric constant $\epsilon_r=2.35-j0.012$) to simulate a typical dielectric coating since, when melted, beeswax fills such cracks or slots completely. Accordingly, the differences in the images of FIGS. 10A and 10B are due to the fact that the filled slot 18 has different microwave properties since it is considered to be a cavity fed by a waveguide as discussed in Zoughi, R., S. Ganchev, C. Huber, H. Abiri, E. Ranu and R. Runser, "A Novel Microwave Method for Filled and Covered Surface Crack Detection in Steel Bridge Members Including Crack Tip Identification," Federal Highway Administration, Grant No. DFTH61-94-X-00023, August 1995, herein incorporated by reference.

It is important to note that in using either the image of FIG. 10A or that of FIG. 10B, the location of the crack tip 72 was estimated within 1 mm of the actual tip location on the aluminum plate.

Figure 9B:
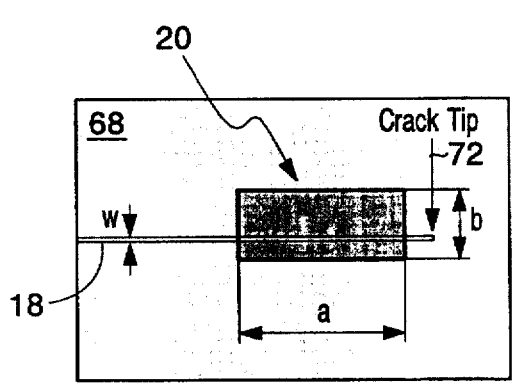
Figure 9C:
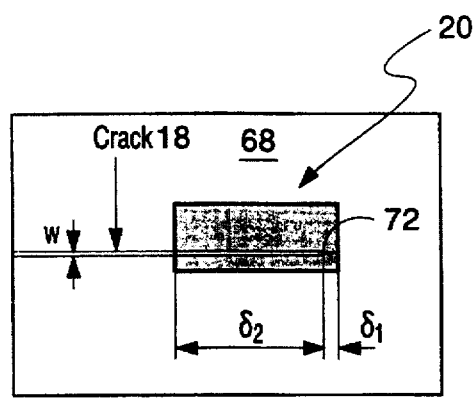

In the second mode for determining a crack tip location, assuming a crack 18 has been detected, the waveguide aperture 20 may be placed on the crack as shown in FIG. 9B. Note that for this mode, it is sufficient that the crack 18 be located somewhere in the middle of the narrow dimension, b, of the waveguide aperture 20. With respect to locating the crack 18 relative to the waveguide aperture 20, it is preferable that the crack 18 be parallel, or substantially parallel, to the wider or broad dimension of the waveguide aperture 20. This alignment can be achieved by, for example, observing a voltage related output based on the signal generated by the sensor 24. More specifically, the voltage related output changes when the crack 18 is within the waveguide aperture 20. The magnitude of this voltage is believed to depend on the alignment of the aperture 20 relative to the crack 18. That is to say, the value of the voltage related output is different from other values when the wider or broad dimension of the aperture 20 is parallel, or substantially parallel, to the length of the crack, such as being a greater voltage when such parallelism exists. For example, when the wider dimension of the aperture 20 is at an angle, such as 45°, relative to the length of the crack 18, the voltage related value is less than the voltage value when the broad dimension of the aperture 20 is parallel, or substantially parallel, to the crack length.

Figure 9D:
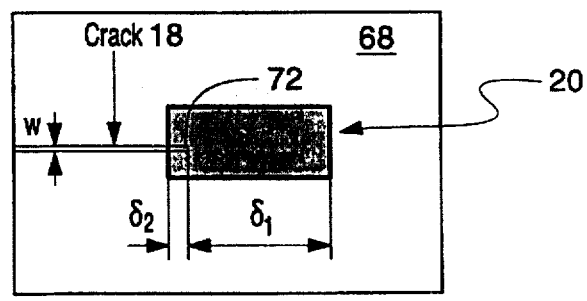
Figure 10A:
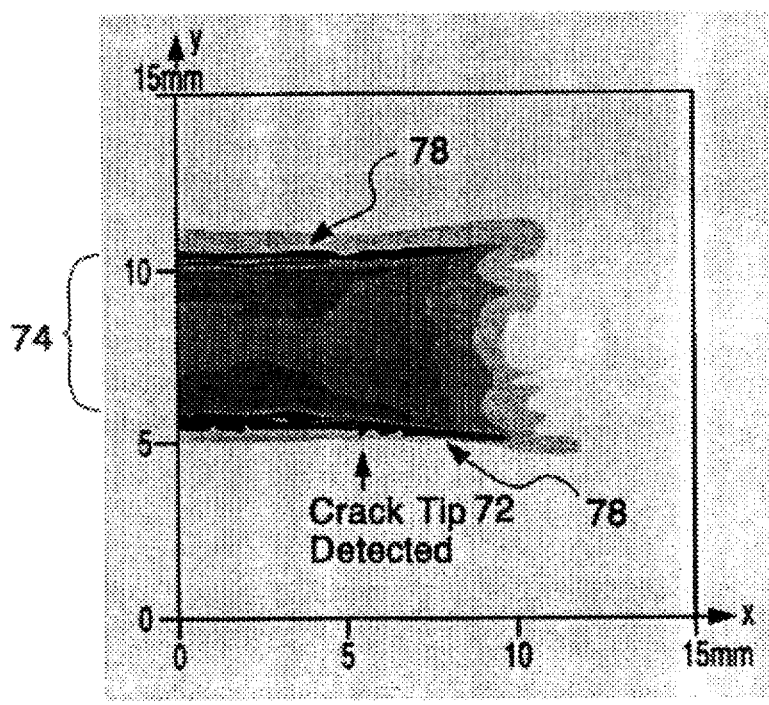
FIG. 10A presents a two-dimensional image of voltage changes when an empty crack is scanned as in FIG. 9A.
Figure 10B:
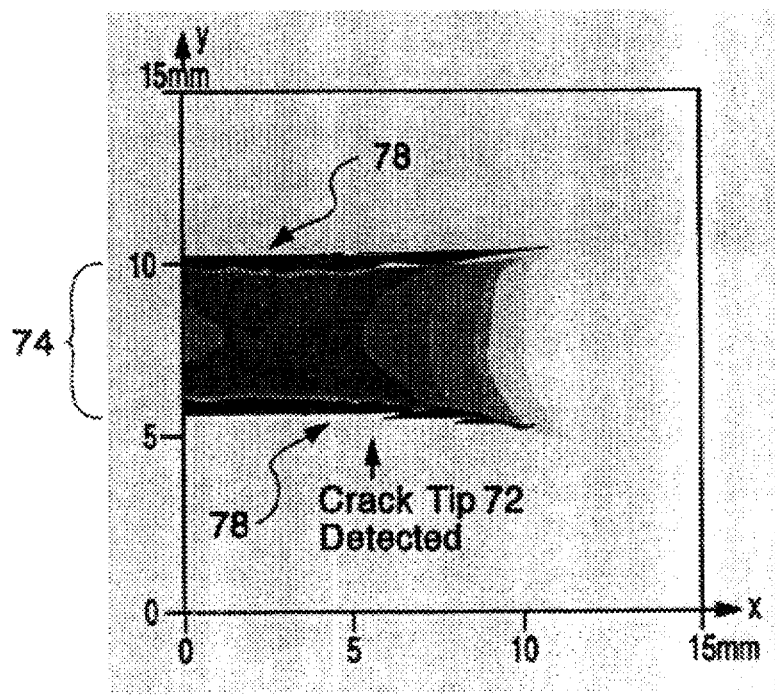
FIG. 10B presents a two-dimensional image of voltage changes when a filled crack is scanned as in FIG. 9A.
Figure 11:
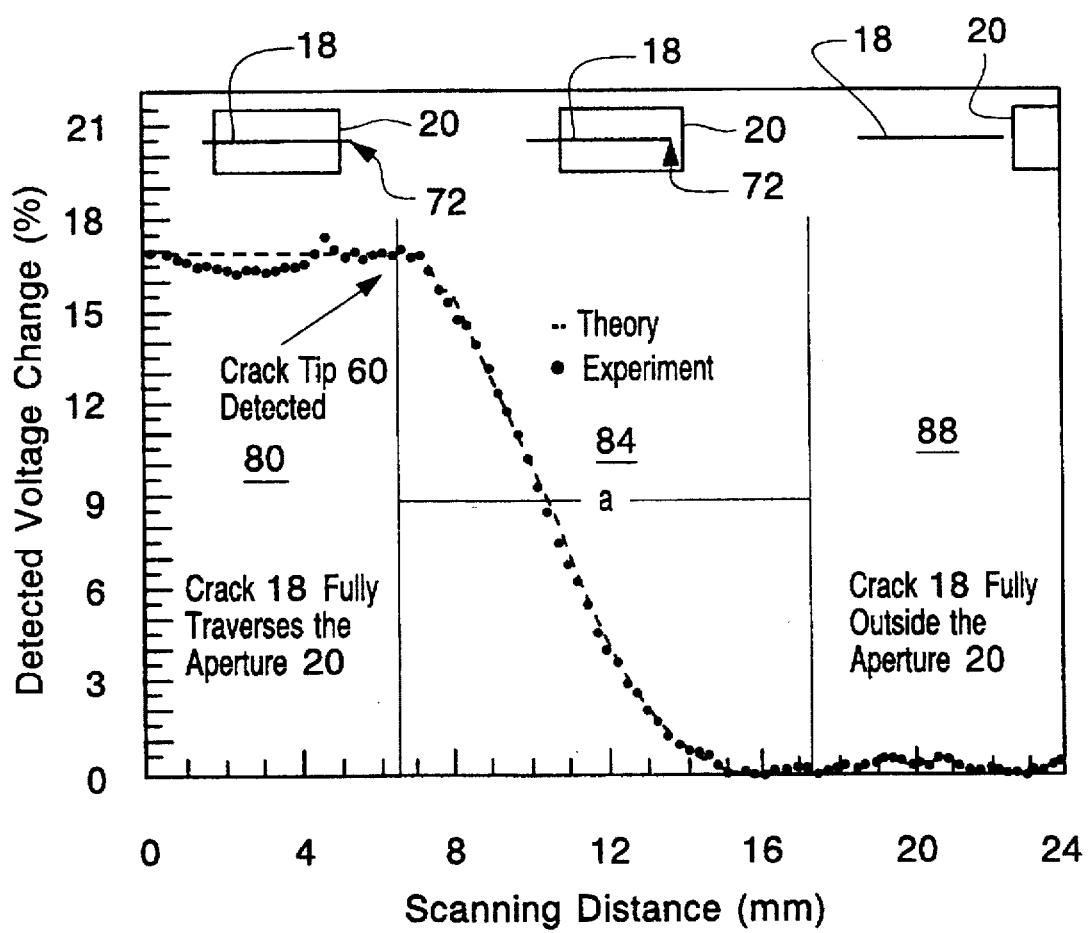
FIG. 11 presents graphs of two crack tip characteristic signals, one determined theoretically and the other determined experimentally for a crack with width W=0.51 mm, depth D=1.5 mm detected at 24 GHz.

After positioning the waveguide aperture 20 so that the crack 18 is within the aperture 20, by moving the waveguide 14 only along the x direction (i.e., along the length of the crack 18 as depicted sequentially in FIGS. 9B through 9D), initially the crack 18 entirely traverses the aperture 20. However, as the tip 72 enters the aperture 20, there is a significant change in the detected signal. Moreover, as the crack tip 72 continues to move further inside the aperture 20, the change in the detected signal gradually changes until the crack tip leaves the aperture. Thus, by recording the detected voltage in the waveguide 14 as a function of the scanning distance along the x direction (i.e., the length of the crack), a "crack tip characteristic detection signal" is obtained that may be used for locating the crack tip 72. As an example of the use of such a crack tip characteristic signal for locating the crack tip 72, consider the graphs of FIG. 11 representing crack tip characteristic signals. The vertical axis of FIG. 11 is measured in terms of the percent of the absolute difference between the voltages detected by the probe 23 (while scanning along the length of the crack 18) and a reference voltage obtained, for example, when the crack 18 is entirely outside the aperture 20. Moreover, the x axis of FIG. 11 measures the distance traveled along the length of the crack 18 from some initial aperture 20 position wherein the crack fully traverses the aperture. Accordingly, FIG. 11 shows the graph of the crack tip characteristic signal for a slot (i.e., a crack) with a width of W=0.51 mm and a depth of D=1.5 mm at 24 GHz. In particular, two graphs are shown in FIG. 11: a graph indicated by dots showing an experimentally generated crack tip characteristic signal, and a second graph indicated by dashes that was generated using a theoretical model describing the interaction of the crack 18 with an open ended rectangular waveguide.

There are three distinct regions to the graphs of FIG. 11: (a) a region 80 wherein the crack 11 entirely traverses the aperture 20; (b) a region 84 wherein the crack tip 72 is within the aperture 20; and (c) a region 88 wherein the crack tip 18 is entirely outside of the aperture (a pictorial representation of each of these regions is provided in the upper part of FIG. 11). The vertical line delineating the boundary between the region 80 and the region 84 indicates the location of the crack tip 72. In particular, this vertical line is an estimate of where the crack tip 72 entered the aperture 20 (alternatively, the rightmost of the vertical lines is an estimate of where the crack tip 72 exited the aperture 20; however, this estimate is less accurate). Thus, the distance between these two vertical lines is substantially equal to the broad dimension, a, of the waveguide aperture 20. The graphs of FIG. 11 indicate that when the crack 18 fully traverses the aperture 20, the detected voltage change is relatively constant. However, as soon as the crack tip 72 enters the aperture 20, this detected voltage change abruptly decreases and continues to decrease while the crack tip 72 moves along the length of the aperture. Subsequently, when the crack tip 72 comes near to the opposite side of the waveguide aperture (approximately 3 mm away in the present case, which is about a third of the broad dimension of the aperture), there is substantially no variation in the detected voltage change. As can be seen, there is excellent agreement between the theoretical and the experimental results. Additionally, using the results of this experiment and many similar such experiments (for different crack dimensions), it is believed that a crack tip 72 location may be estimated accurately to within 0.25 mm of its actual location (using a waveguide 14 with dimensions of a=10.67 mm and b=4.32 mm at a frequency of 24 GHz), wherein 0.25 mm is the scan step size used along the crack length to obtain the results shown in FIG. 11. That is, the crack tip 72 is located within an area of about 1 $mm^2$ which is substantially smaller than the aperture 20. Furthermore, it is believed that an even finer scan step size results in a more accurate crack tip 72 location estimate.

Figure 12:
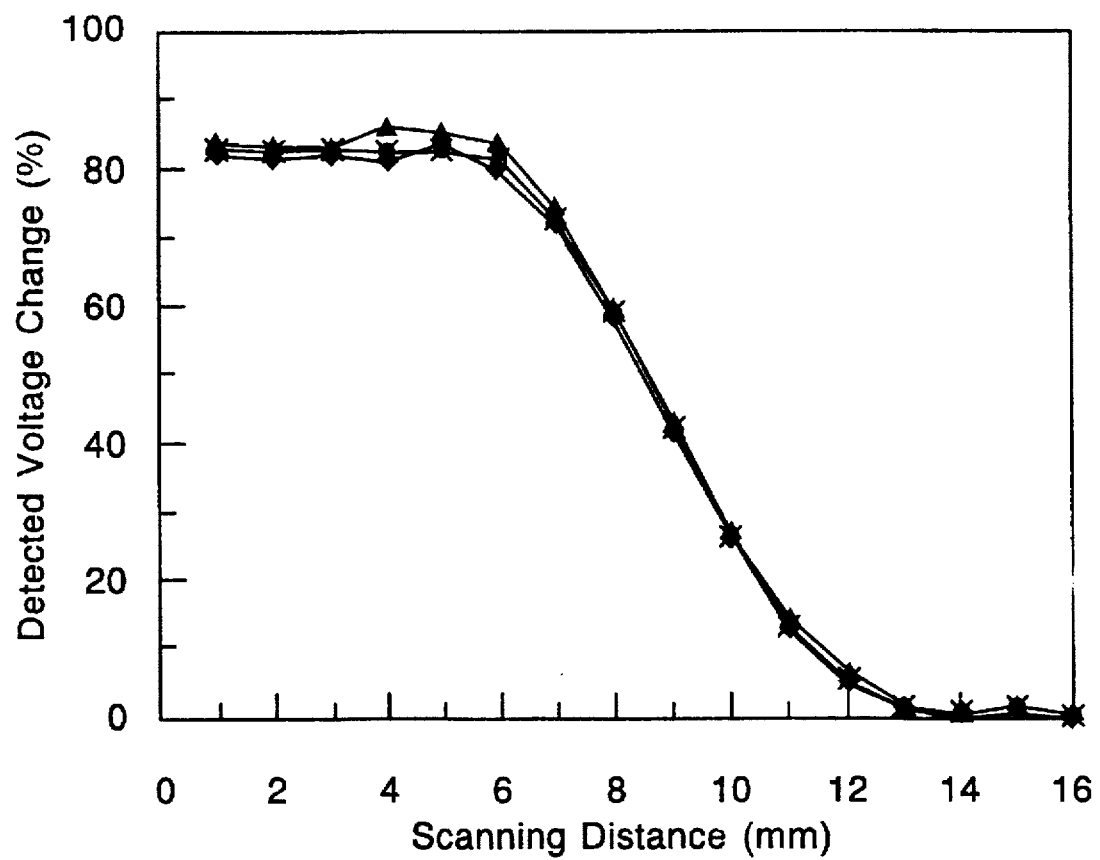
FIG. 12 presents the crack tip characteristic signal graphs for a crack with W=0.58 mm, D=2 mm, measured at 24 GHz at four positions (each 0.5 mm apart) around the middle of the narrow dimensions of the waveguide aperture.

The practical usefulness of the present invention is enhanced by the fact that the placement of the crack 18 exactly in the middle of the narrow dimension, b, of the aperture 20 is not necessary for identifying the location of the crack tip 72 with the present invention. For example, note that FIG. 5 shows that as long as the crack 18 is within the narrow dimension of the aperture 20 (excluding being right at the aperture edges), the detected voltage remains fairly constant (i.e., the middle portion 34). To further illustrate this fact, a crack tip characteristic signal for a crack 18 with a width of W=0.58 mm and a depth of D=2.0 mm was obtained at 24 GHz while placing the crack 18 at four different positions around the middle of the narrow dimension, b, of the aperture 20 (i.e., at positions 0.5 mm apart, wherein the aperture 20 dimensions are a=10.67 mm and b=4.32 mm). Graphs of the corresponding crack tip characteristic signals are shown in FIG. 12. The results in this Figure show substantial consistency. Thus, no special equipment is needed to center the crack 18 within the aperture 20 to accurately and reliably practice the present invention.

Figure 13:
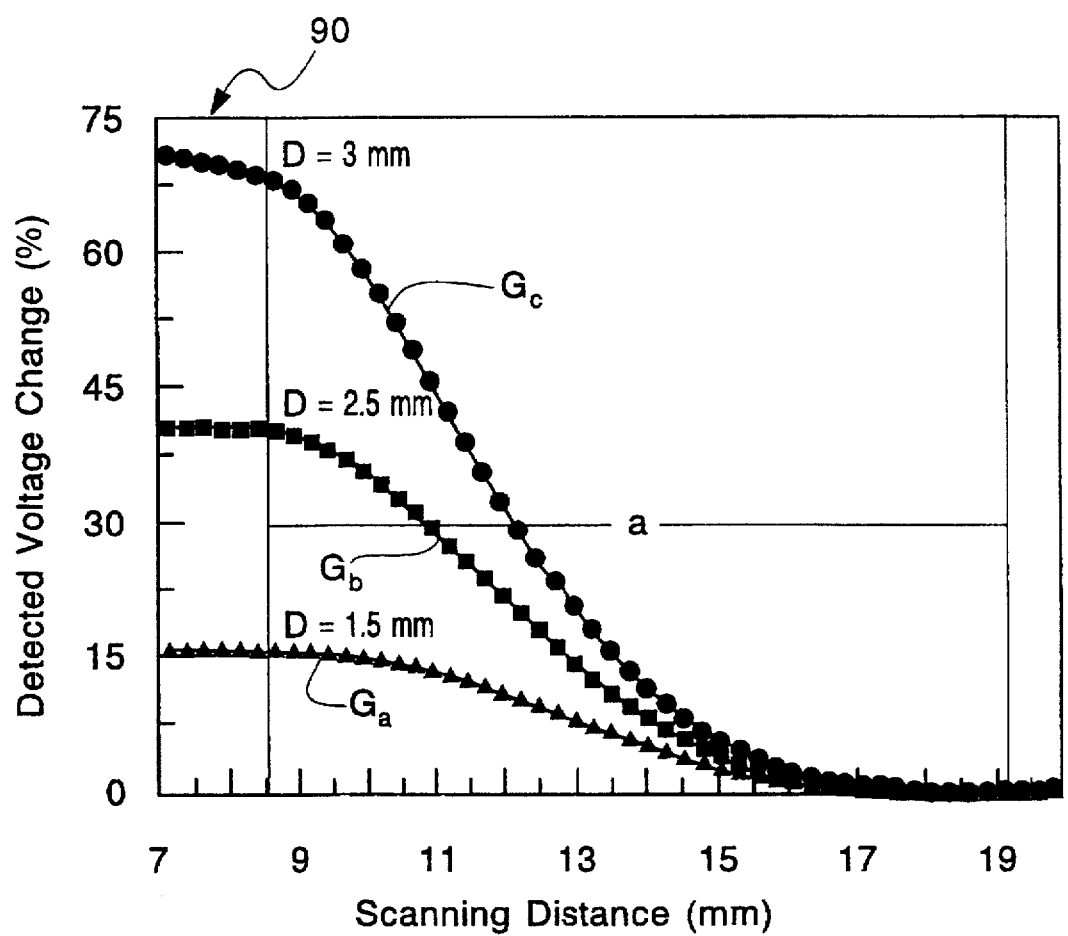
FIG. 13 presents the crack tip characteristic signal graphs for three cracks with equal widths of W=0.51 mm and different depths at 24 GHz.

FIG. 13 shows the graphs $G_a$, $G_b$ and $G_c$ of the crack tip characteristic signal recorded at 24 GHz, for three cracks 18a, 18b and 18c (not shown) with equal widths of W=0.51 mm and depths of D=1.5 mm, 2.5 mm and 3.5 mm, respectively (wherein the aperture 20 dimensions are a=10.67 mm and b=4.32 mm). Thus, just as illustrated in FIG. 3, crack depth variations cause a change in the level of the detected signal when the crack 18 entirely traverses the waveguide aperture. Likewise, for all three cases graphed in FIG. 12, the short circuit level is the same (e.g., the detected voltage change when scanning at distances greater than 19.5 mm). However, the voltage change, i.e., signal level change, for the three different cracks, when fully traversing the waveguide aperture 20 is different (i.e., for region 90 where the scanning distance is between 7 mm and 8.5 mm). Accordingly, the accuracy of a crack tip location estimate depends on the difference between the short circuit signal (i.e., when the crack is outside of the aperture 20) and the signal level when the crack 18 entirely traverses the aperture. For example, for graph $G_a$, the crack tip 72 may be estimated within approximately 1.25 mm of its actual location whereas for graph $G_c$, the crack tip 72 may be estimated within 0.25 mm of its actual location. However, note that if the crack tip characteristic signal for graph $G_a$ is plotted using a finer scale for the scanning distance step size, then the location of the abrupt change indicating the crack tip, may be estimated within approximately 0.25 mm of the actual crack tip location. Alternatively, once the crack 18 is detected, a higher resolution for detecting the abrupt change in the crack characteristic signal may be obtained by adjusting the operating frequency or the probe 23 position and thereby enhancing the signal difference between the two extreme signal levels of the crack tip characteristic signal.

Figure 14:
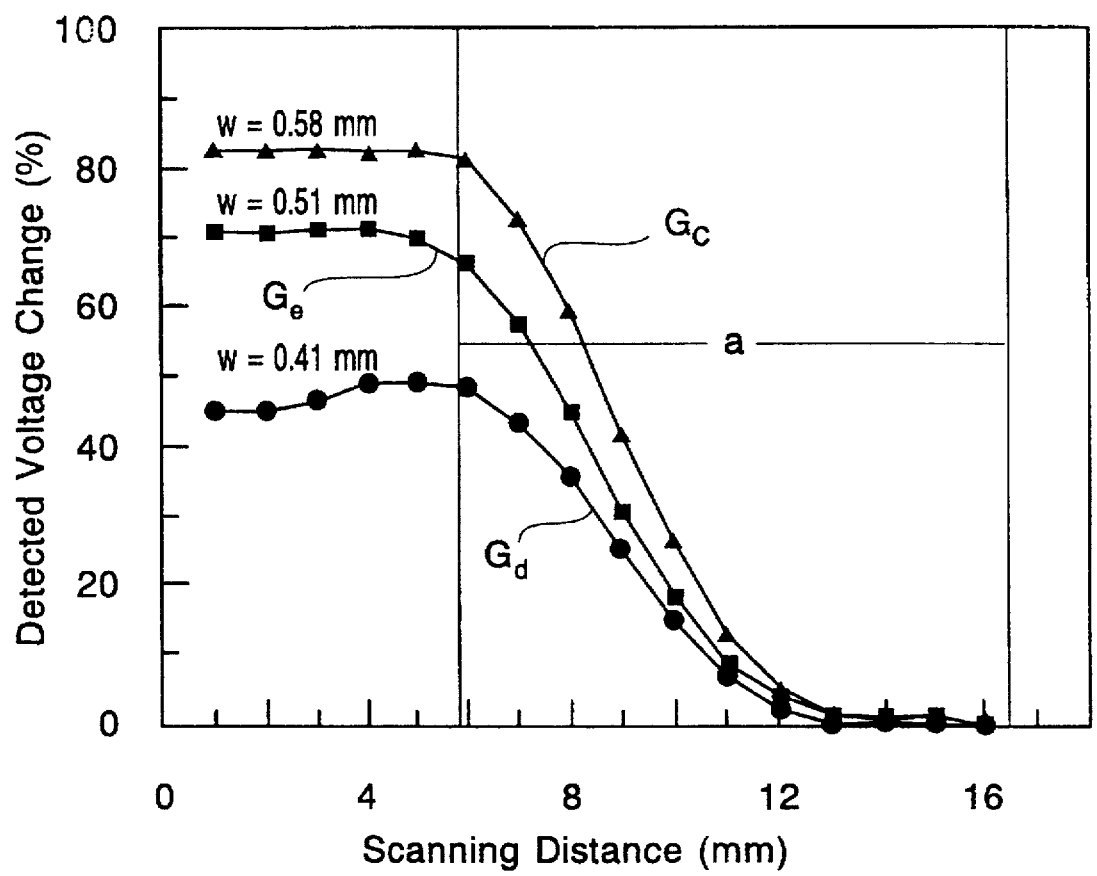
FIG. 14 presents the crack tip characteristic signal graphs for three cracks with equal depths of D=2 mm and different widths a 24 GHz.

FIG. 14 presents graphs $G_d$, $G_e$ and $G_f$ of crack tip characteristic signals for three cracks 18d, 18e and 18f (not shown), recorded at 24 GHz with equal crack depths of D=2 mm and widths of W=0.41 mm, 0.51 mm and 0.58 mm, respectively (wherein the aperture 20 dimensions are a=10.67 mm and b=4.32 mm). For these cracks, the crack tip locations were estimated to within approximately 1 mm, this being the scan step size for the measurements of these graphs. As in the previous cases, the larger the difference is between the signal levels when the crack 18 is entirely outside the aperture 20 and when the crack entirely traverses the aperture, the more accurate a crack tip 72 location estimate becomes.

FIG. 15 shows the graphs $G_g$ and $G_h$ of the crack tip characteristic signals, recorded at 24 GHz (and with the aperture 20 having dimensions a=10.67 mm and b=4.32 mm) for a crack 18 with a width of W=0.3 mm and a depth of D=2 mm, wherein the crack was filled with beeswax for obtaining the graph $G_g$ and wherein the crack was empty for obtaining the graph $G_h$. These graphs illustrate the observation that when a crack 18 is filled with a dielectric, its apparent or "electrical" depth changes. That is, the crack tip characteristic signal for a filled crack, in comparison to an empty crack, may be similar to a crack whose depth is larger as was shown in FIG. 13. Accordingly, a dielectrically filled crack may provide a more accurate estimate for a crack tip 72 than an empty crack.

Figure 16:
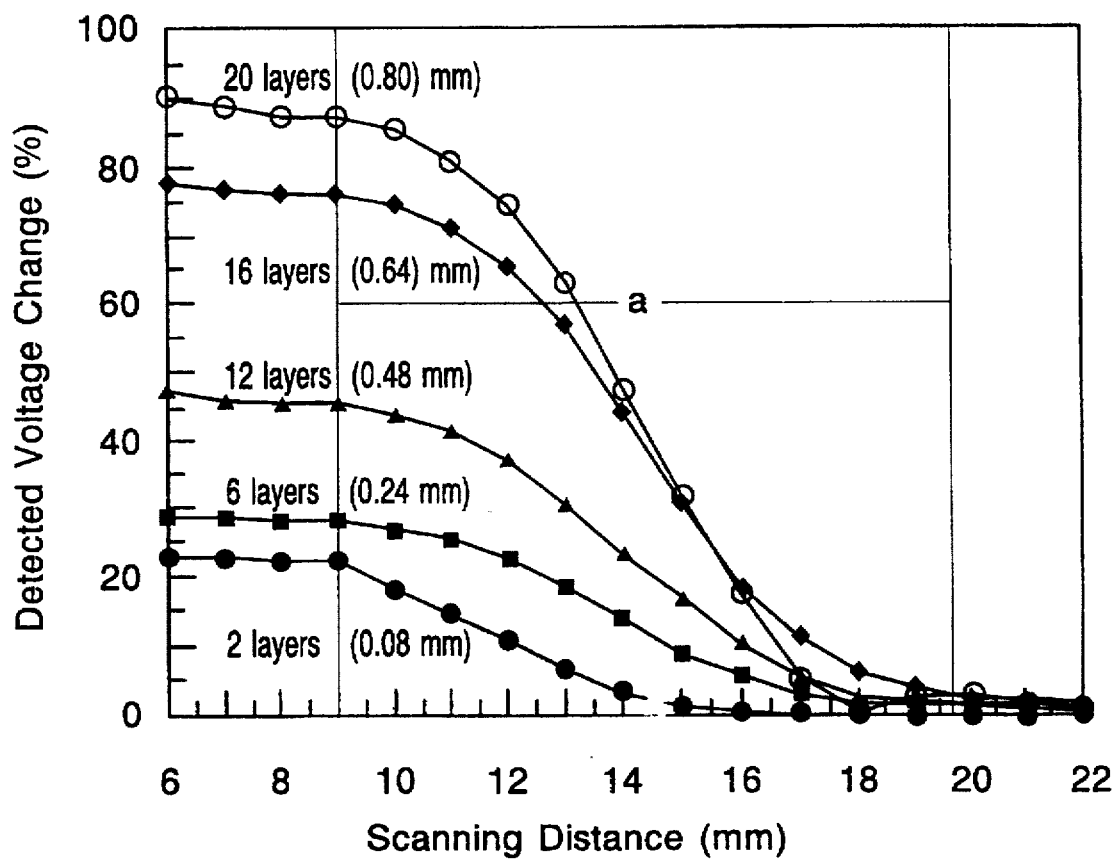
FIG. 16 presents the crack tip characteristic signal graph for a crack with W=0.51 mm and D=1.5 mm at 24 GHz, covered with 2 layers (0.08 mm), 6 layers (0.24 mm), 12 layers (0.48 mm), 16 layers (0.64 mm) and 20 layers (0.8 mm)

In FIG. 16, graphs of crack tip characteristic signals for covered cracks 18 are shown. In particular, graphs for crack tip characteristic signals of a crack 18 with a width of W=0.51 mm and a depth of D=1.5 mm, recorded at 24 GHz (and with the aperture 20 having dimensions a=10.67 mm and b=4.32 mm) are provided when the crack was covered with various layers of wrapping paper for simulating various paint thicknesses in that wrapping paper and common paint have similar dielectric properties. More precisely, the crack tip characteristic signal was measured for the crack when it was covered with: (a) two sheets of wrapping paper having a total thickness of 0.08 mm, (b) six sheets of wrapping paper having a total thickness of 0.24 mm, (c) 12 sheets of wrapping paper having a total thickness of 0.48 mm, (d) 16 sheets of wrapping paper having a total thickness of 0.64 mm, and (e) 20 sheets wrapping paper having a total thickness of 0.8 mm. It is observed from the graphs that the relatively abrupt transition around 9 mm persists for all coating thicknesses. Accordingly, for each of these covered crack cases, the accuracy by which the crack tip 72 may be located is estimated to be within approximately 2 mm of its actual position. Furthermore, the accuracy of determining covered crack tip locations may also be improved by adjusting the microwave operating frequency and the position of the probe 23.

Figure 17:
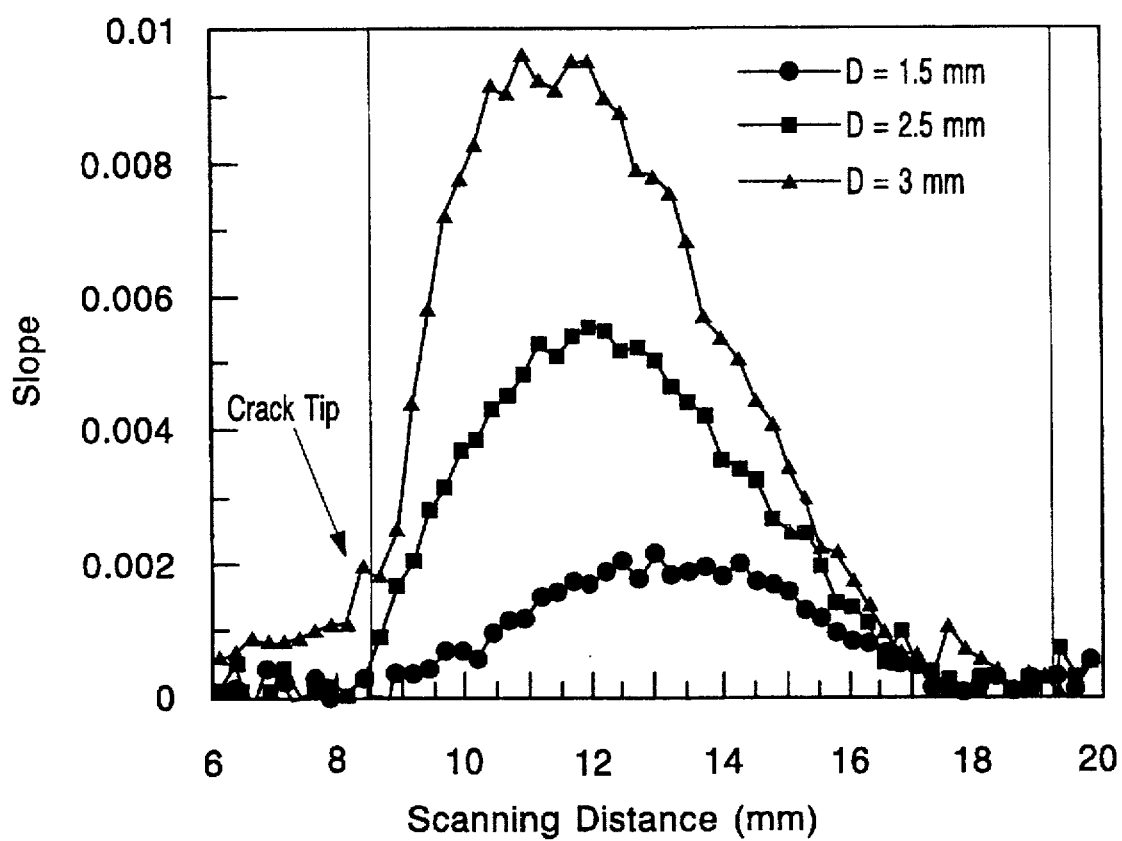
FIG. 17 presents the forward point-to-point slope calculated for the cracks shown in FIG. 14.

The results presented hereinabove do not include any post data processing or analysis methods. It is believed that even simple data processing techniques such as a forward difference method for gradient approximation (i.e., calculating a forward slope for every data point) may be used to analyze the data from detector 10 and thereby improve the accuracy of estimating a crack tip 72. Toward this end, FIG. 17 shows the forward difference method calculated for each point of the data shown in FIG. 13. Thus, using this approach, the crack tip 72 location is estimated by determining when the slope of these graphs begin to change substantially.

With regard to an operator or user obtaining and using information related to a crack tip location, the waveguide aperture 20 housing or walls, in one embodiment, can be relied upon. In such a case, upon the operator observing or visualizing a voltage related difference in value due to the crack length no longer being fully within the waveguide aperture 20, the operator can stop movement of the waveguide aperture 20 and use this wall or edge as a guide to locate the crack tip. More specifically, the difference in voltage occurs over a relatively very small distance (e.g., 1–4 mm). Consequently, the wall defining the waveguide aperture 20 is very close to the crack tip when this change in voltage is observed by the operator. The operator is able to note or mark this location and, if not essentially over the crack, such a marking is within a very short, acceptable distance from the exact location of the crack tip. Once the crack tip is marked or identified in this manner, appropriate steps can be taken to alleviate or otherwise correct for the undesired crack in the surface by, for example, making or drilling a hole in or adjacent to the crack tip in order to stop the spreading of the crack. In one embodiment, the operator is able to use a relatively small drill, such as a ¼-inch diameter drill bit, that would readily encompass the crack tip.

The above disclosure sets forth a number of embodiments of the present invention. Other arrangements or embodiments, not precisely set forth, could be practiced under the teachings of the present invention and as set forth in the following claims.

What is claimed is:

1. A method for measuring one or more crack dimensions in a microwave reflective surface, comprising:

transmitting a microwave first signal;

reflecting said first signal from said microwave reflective surface to produce a second signal;

detecting a crack using at least one of said first signal and said second signal obtained by a microwave receiving device;

moving said microwave receiving device relative to the crack; and determining information related to at least one of a first tip, a width and a depth of the crack, after said moving step, and in which said determining step includes at least one of the following:

analyzing a number of voltage related values obtained using said microwave receiving device during said moving step, when determining the presence of the first tip of the crack, relying on at least one dimension of said microwave receiving device and at least two voltage related values obtained using said microwave receiving device during said moving step, when determining the width of the crack, and scanning across a width of the crack using said microwave receiving device and analyzing at least one voltage related value obtained while scanning, when determining the depth of the crack.

2. A method, as claimed in claim 1, when determining information related to the first crack tip, wherein:

said determining step includes obtaining a length of the crack based on a determination of the location of the first crack tip and a second crack tip.

3. A method, as claimed in claim 1, wherein:

said microwave receiving device has a microwave receiving area with a longitudinal extent and a lateral extent and, when information related to the crack tip is being determined, the determining step includes:

positioning said longitudinal extent of the device such that a length of the crack extends throughout all of said longitudinal extent of said microwave receiving area;

obtaining a first voltage related value based on a first position of said microwave receiving area;

changing said microwave receiving area position such that the crack length does not extend throughout said longitudinal extent of said microwave receiving area;

obtaining a second voltage related value based on a second position of said microwave receiving area after said changing step; and ascertaining a location of the first crack tip using at least said first and second voltage related values.

4. A method, as claimed in claim 1, wherein:

said moving step includes, when information related to the crack tip is being determined, aligning said microwave receiving device relative to a length of the crack.

5. A method, as claimed in claim 4, wherein said microwave receiving device includes a microwave receiving area having a longitudinal extent and a lateral extent and said aligning step includes:

adjusting said longitudinal extent of said microwave receiving area such that it is substantially parallel to the crack length.

6. A method, as claimed in claim 1, when information related to the first crack tip is being determined, wherein:

said determining step includes identifying a position of the first crack tip using a wall of said microwave receiving device.

7. A method, as claimed in claim 6, wherein:

said identifying step includes using an edge of said wall of said microwave receiving device.

8. A method, as claimed in claim 1, wherein:

said determining step is conducted while the depth of the crack is filled to at least one-half with material.

9. A method, as claimed in claim 3, wherein:

said determining step is conducted while said longitudinal extent of said microwave receiving area is different from substantially parallel to the crack length and a voltage related value is obtained that is less than a voltage related value that is obtained when said longitudinal extent is substantially parallel to the crack length.

10. A method, as claimed in claim 1, when determining information related to the width of the crack, wherein:

said determining step includes obtaining magnitudes of a third signal related to said first and second signals during said moving step, identifying positions associated with two extrema of said magnitudes, ascertaining a distance between said identified positions and using at least said ascertained distance and a dimension of said microwave receiving device to determine the width of the crack.

11. A method, as claimed in claim 1, when determining information related to the depth of the crack, wherein:

said determining step includes using information related to crack widths that was obtained before said detecting step.

12. A method, as claimed in claim 1, when determining information related to the depth of the crack, wherein:

said determining step includes obtaining a third signal related to said first and second microwave signals while moving said microwave receiving device relative to the crack.

* * * * *